(12) United States Patent
Riley et al.

(10) Patent No.: US 6,217,835 B1
(45) Date of Patent: Apr. 17, 2001

(54) STERILIZATION CONTAINER

(75) Inventors: Edward D. Riley, Falmouth, ME (US); Ansgar Brossard, Krailling (DE)

(73) Assignee: Riley Medical, Inc., Auburn, ME (US)

( * ) Notice: Subject to any disclaimer, the term of this patent is extended or adjusted under 35 U.S.C. 154(b) by 0 days.

(21) Appl. No.: 09/276,045

(22) Filed: Mar. 25, 1999

Related U.S. Application Data

(63) Continuation-in-part of application No. 09/052,191, filed on Mar. 31, 1998, now Pat. No. 6,048,503.

(51) Int. Cl.[7] .................................. A61L 2/26; E05C 5/00
(52) U.S. Cl. .......................... 422/297; 422/299; 422/300; 206/807; 206/370; 206/1.5; 220/265; 220/324; 220/835; 292/63; 292/71; 292/113; 292/162; 292/169; 292/307 A
(58) Field of Search ........................... 422/26, 297, 298, 422/299, 300; 206/363, 370, 439, 1.5, 807; 220/265, 315, 324, 833, 834, 835; 292/162, 113, 307 A, 307 B, 315, 169, 32, 71, 63, 156

(56) References Cited

U.S. PATENT DOCUMENTS

| | | |
|---|---|---|
| 4,331,257 * | 5/1982 | Taschner . |
| 4,617,178 | 10/1986 | Nichols . |
| 4,625,885 | 12/1986 | Nichols . |
| 4,716,025 | 12/1987 | Nichols . |
| 4,728,504 | 3/1988 | Nichols . |
| 4,752,453 | 6/1988 | Nichols . |
| 4,900,519 | 2/1990 | Nichols . |
| 4,915,913 * | 4/1990 | Williams et al. . |
| 4,915,918 | 4/1990 | Nichols . |
| 5,011,718 | 4/1991 | Patterson . |
| 5,065,885 * | 11/1991 | Scaroni et al. . |
| 5,080,874 | 1/1992 | Nichols . |
| 5,183,643 | 2/1993 | Nichols . |
| 5,202,098 | 4/1993 | Nichols . |
| 5,227,074 | 7/1993 | Nichols et al. . |
| 5,324,489 | 6/1994 | Nichols et al. . |
| 5,328,661 * | 7/1994 | Taschner . |
| 5,348,180 * | 9/1994 | Shepard . |
| 5,370,254 * | 12/1994 | Hardigg et al. . |
| 5,382,528 * | 1/1995 | Scoville . |
| 5,474,738 | 12/1995 | Nichols et al. . |
| 5,508,006 * | 4/1996 | Gabele et al. . |
| 5,626,373 * | 5/1997 | Chambers et al. . |
| 5,630,507 * | 5/1997 | Baker . |
| 5,887,745 * | 3/1999 | Wood . |

* cited by examiner

Primary Examiner—Deborah Jones
Assistant Examiner—Jennifer McNeil
(74) Attorney, Agent, or Firm—Cesari and McKenna

(57) ABSTRACT

A sterilization container for medical instruments includes a receptacle with a bottom wall and an open top, there being a multiplicity of vent openings in the bottom wall. The receptacle has a cover movable between a closed position wherein the cover closes the open top of the receptacle and an open position wherein the cover is positioned to allow access to the interior of the receptacle. A filter sheet is positioned in the receptacle so as to cover the bottom wall and the vent openings therein and the receptacle contains one or more trays for supporting medical instruments above the filter sheet. A perforated highly thermally conductive plate is positioned between the trays and the filter sheet so that when steam enters the container through the vent openings during steam sterilization, it heats the plate to a temperature sufficient to revaporize steam condensate collecting on the plate. The internal structure of the container is also disclosed.

7 Claims, 5 Drawing Sheets

STERILIZATION CONTAINER

RELATED APPLICATION

This application is a continuation-in-part of Ser. No. 09/052,191, filed Mar. 31, 1998, now U.S. Pat. No. 6,048,503.

BACKGROUND OF THE INVENTION

1. Field of the Invention

This invention relates to a sterilization container. It relates more particularly to a container for medical instruments and other articles which are to be sterilized by exposure to steam.

Prior to their use, medical and surgical instruments have to be sterilized. This is often done by placing the instruments in a container and inserting the container into an autoclave where the container and its contents are subjected to high temperature steam under pressure. The container is designed to allow steam to enter the container during the sterilization process so that the steam contacts the instruments therein. In some cases, the container is equipped with a valve which opens under the pressure of the steam in the autoclave and which closes following the sterilization process so that the container remains sealed until it is time to use the instruments. Other sterilization containers have permanent vent openings which are covered by a microbial filter. The filter allows steam to enter the container during the sterilization process but has a sufficiently fine structure to prevent the entry of microbes and other contaminants during and after sterilization. The present container is of the latter type.

2. Prior Art

Conventional sterilization containers which incorporate a microbial filter have several disadvantages. Some do not provide enough open space within the container to allow steam to penetrate, and circulate within, the container. Therefore, the sterilization cycle for such containers is relatively long, particularly if the sterilizer or autoclave does not include a vacuum cycle wherein air is drawn from the container prior to the injection of steam into the container. This problem can be alleviated to some extent by including vent openings in more than one wall of the container. However, this solution requires the placement in the container of a corresponding number of filter sheets which increases cost and the time it takes to assemble the container. Other sterilization containers are made of metal and therefore conduct heat efficiently. However, they are heavy and expensive and the heat-sterilized container cannot be handled until after it is cooled off which effectively increases the length of the sterilization cycle.

There do exist sterilization containers made of plastic material. However, those containers are not entirely satisfactory because it has been found that moisture accumulates within the container which moisture tends to wet the filter sheet thereby degrading its effectiveness as a microbial filter. In other such containers, the filter sheet is not sufficiently protected from medical instruments and other components within the container with the result that the sheet is penetrated, again destroying its effectiveness as a filter.

Still further, some prior containers of this general type are not designed to facilitate loading the container with medical instruments in a given order before sterilization so that those instruments will remain in the same position during sterilization and subsequent handling so that when it is time to use the instruments, they can be presented to a surgeon in a desired order for a particular procedure.

Finally, with prior sterilization containers of this general type, one cannot be assured that a sterilized container has remained unopened such that the instruments in the container are still in a sterile condition when it is time to use the instruments.

SUMMARY OF THE INVENTION

Accordingly it is an object of the present invention to provide an improved sterilization container.

Another object of the invention is to provide a container of this type which enhances the sterilization process so that sterilization can be carried out in a minimum amount of time.

A further object of the invention is to provide a sterilization container which prevents the accumulation of moisture within the container.

Yet another object of the invention is to provide a sterilization container which maintains instruments placed in the container at set positions within the container.

A further object of the invention is to provide a container of this type which promotes the circulation of steam within the container during the sterilization process.

Another object of the invention is to provide such a container whose microbial filter is protected against penetration by instruments and other objects within the container.

An additional object is to provide a sterilization container with an improved latching mechanism.

A further object of the invention is to provide a security lock for a container of this type which signals when the container has been unlatched improperly.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, our container includes an open top box-like receptacle having a bottom wall formed with an array of vent openings. A filter sheet is positioned in the receptacle so as to overly the bottom wall and the vent openings therein. Also positioned in the receptacle above the filter sheet is a highly thermally conductive plate having a multiplicity of holes therein which are smaller than the vent openings such that the plate permits the passage of steam into the receptacle space above the plate but prevents objects in the receptacle from contacting the fiber sheet.

The container also includes one or more instrument-supporting trays positioned in the receptacle above the plate. The trays are formed as grids with relatively large through-holes or openings. Those trays are stacked in the receptacle so that their openings are in register whereby a relatively large amount of open space remains in the receptacle, In addition, the container includes a cover which may be closed over the open top of the receptacle to provide a seal between the two, with portions of the trays contacting the underside of the cover so that when the cover is closed, there can be no appreciable vertical movements of the filter, plate and tray(s) within the container.

Preferably, the container is provided with at least one latch which can latch the cover in its closed position and a safety lock releasably attached to the receptacle and cover for preventing each latch from being unlatched without providing a visual indication that such unlatching has occurred. Thus, medical personnel can take an already sterilized container off the shelf and, by observing the safety lock, determine that the container has been opened after sterilization such that the contents of the container are no longer in a sterile condition.

Further as will be described, the interior components of the container are designed to promote efficient and thorough circulation of steam within the container during sterilization and to facilitate proper presentation of instruments that were sterilized in the container when it is time to use those instruments. Specifically, during sterilization, the thermally conductive plate functions as a heat source which re-vaporizes condensate dropping into the plate from the trays and instruments thereon thereby enhancing the sterilization process and preventing the condensate from wetting the filter sheet.

BRIEF DESCRIPTION OF THE DRAWINGS

For a fuller understanding of the nature and objects of the invention, reference should be had to the following detailed description taken in connection with the accompanying drawings, in which.

DETAILED DESCRIPTION OF ILLUSTRATIVE EMBODIMENTS

Figure 1:
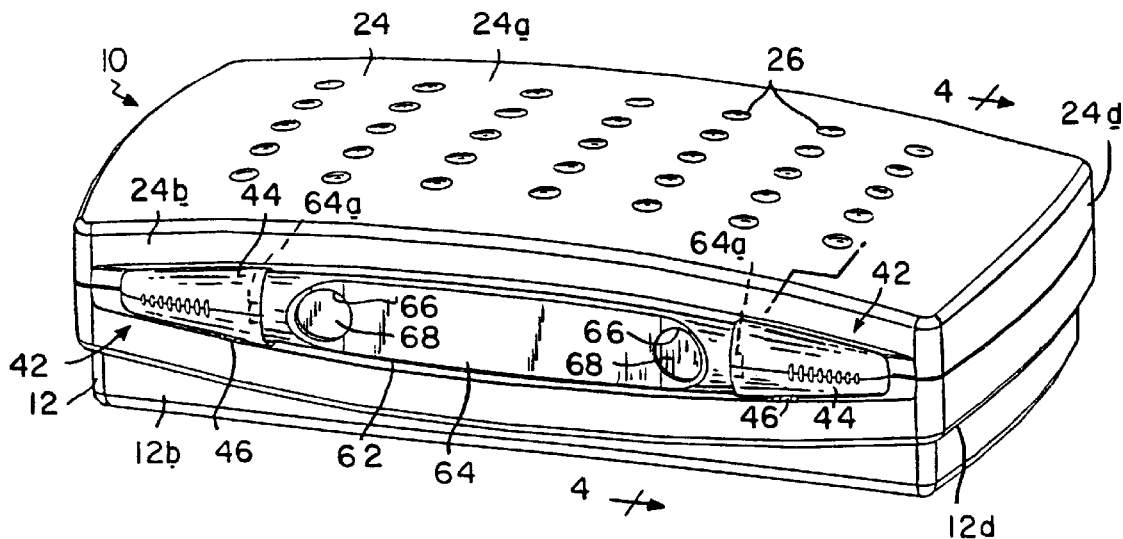
FIG. 1 is a perspective view from above of a sterilization container incorporating the invention shown in its closed condition.
Figure 2:
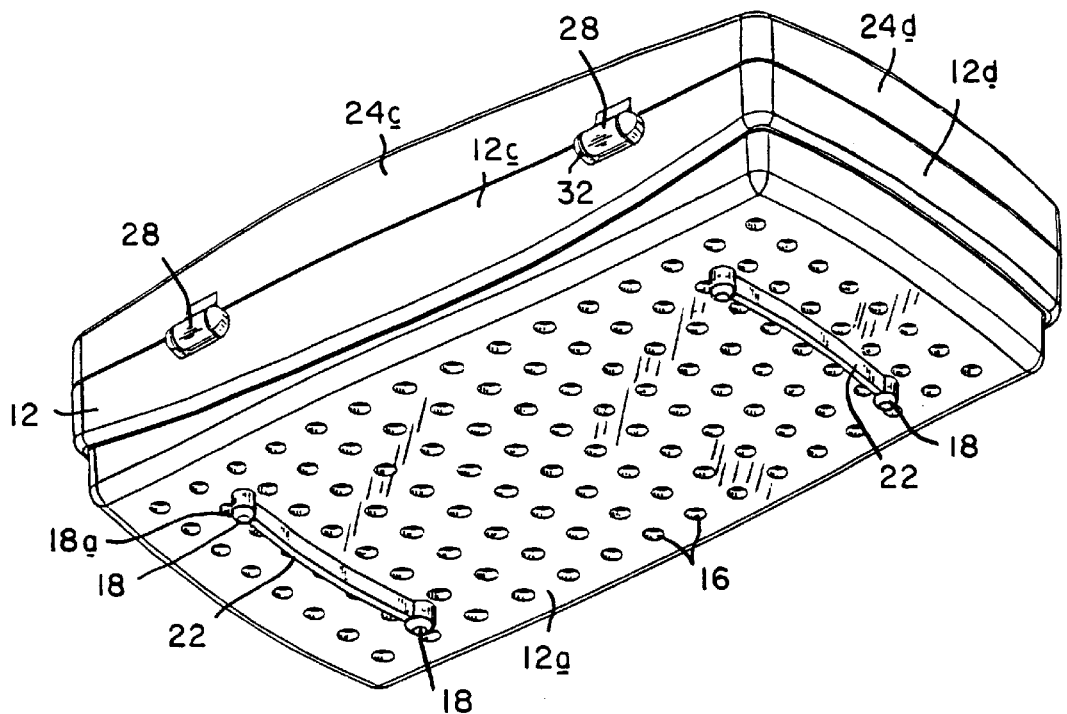
FIG. 2 is a perspective view from below thereof.

Referring to FIGS. 1 and 2 of the drawings, our container comprises a housing indicated generally at 10 made of a rugged, impact resistant, medical grade; transparent plastic material. The housing is composed of a generally rectangular receptacle 12 having a bottom wall 12a, a front wall 12b, a rear wall 12c and a pair of mirror-image end walls 12d all extending up from the bottom wall 12a to form an open top box-like structure. As beset seen in FIG. 2, an array of vent openings 16, each being about ⅜in. in diameter, is provided in bottom wall 12a, these openings being distributed in columns and rows over substantially the entire area of the bottom wall. Also, pairs of front and rear legs 18 extend down from the bottom wall adjacent opposite ends of receptacle 12, each pair of legs being connected by a depending rib 22 which is specially curved as will be described in more detail later.

Housing 10 is provided with a rectilinear cover 24 which is shaped and arranged to close the open top of receptacle 12. Cover 24 includes a top wall 24a, a front wall 24b, a rear wall 24c and a pair of mirror image end walls 24d. As best seen in FIG. 1, the cover is preferably transparent so that one can see into the housing and its top wall 24a is provided with an array of dimples 26 arranged in columns and rows over the area of top wall 24a.

Figure 3:
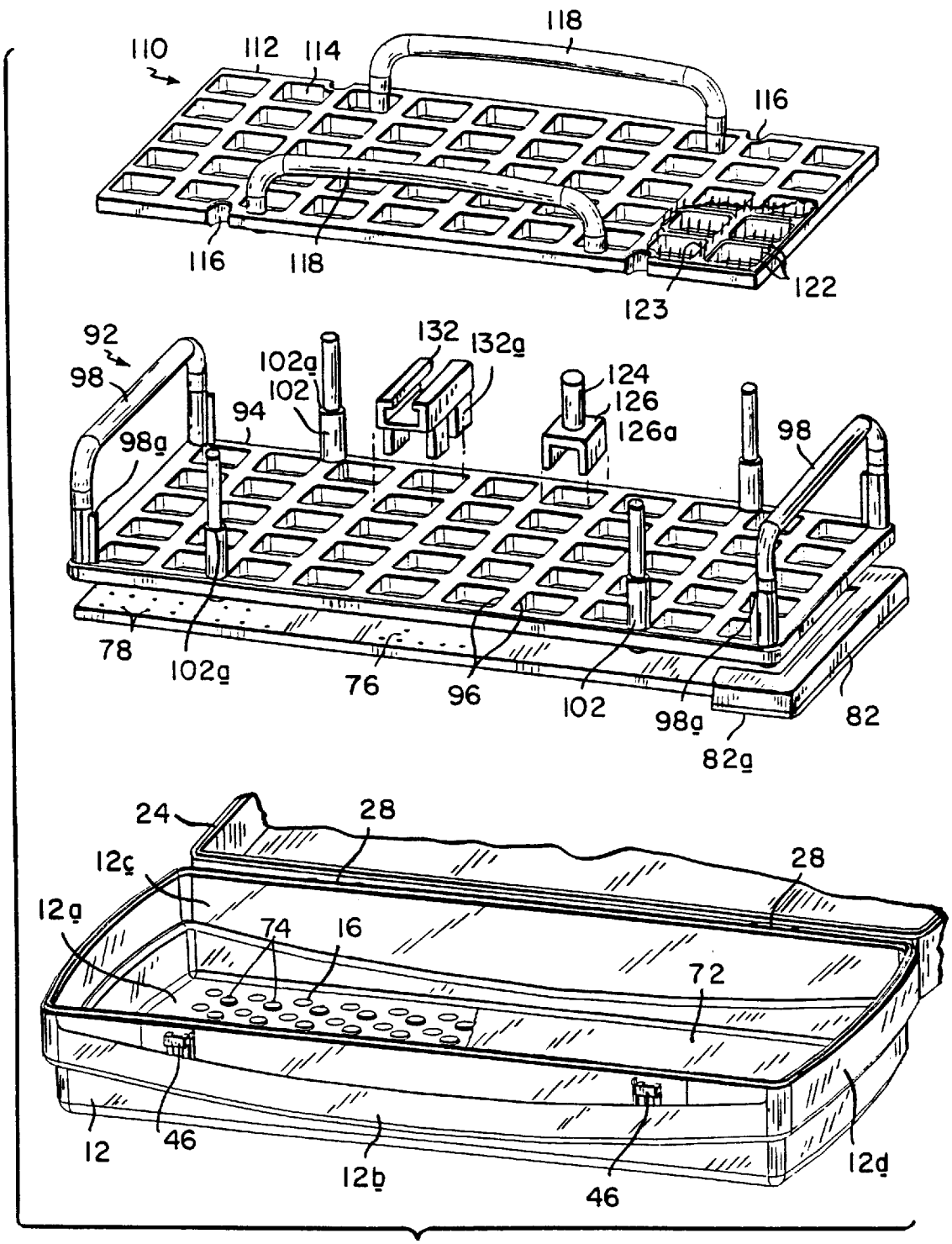
FIG. 3 is an exploded perspective view showing the interior components of the open container in greater detail.

Cover 24 is hinged to receptacle 12 by hinges 28 at the rear walls 12c, 24c of those members so that the cover can be swung between a closed position shown in FIGS. 1 and 2 wherein the cover completely closes the open top of receptacle 12 and an open position shown in FIG. 3 wherein the cover is swung rearwardly so as to expose the interior of receptacle 12.

Figure 4:
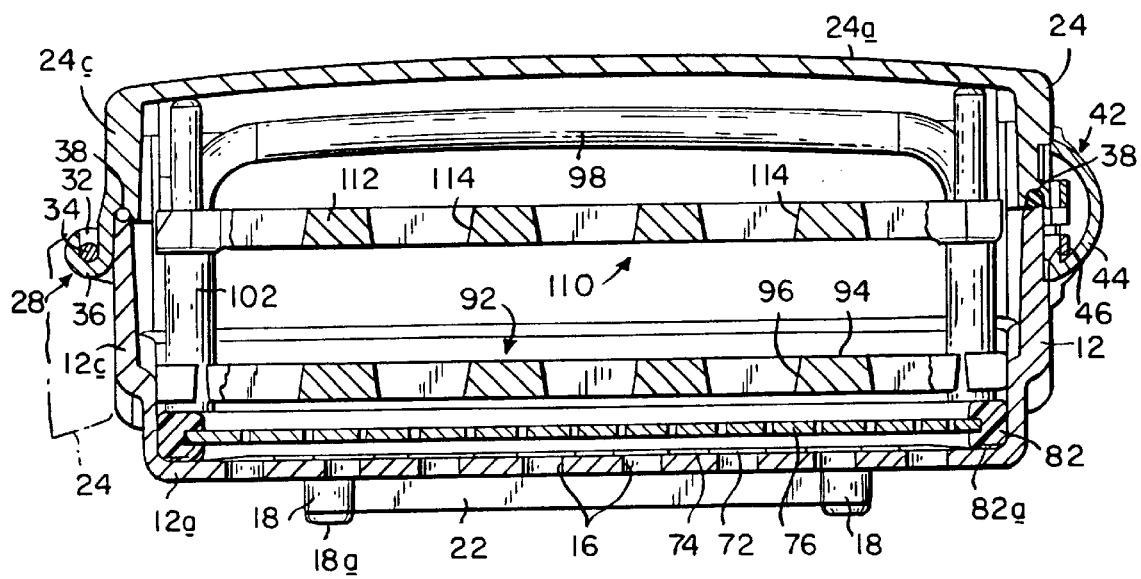
FIG. 4 is a sectional view taken along line 4—4 of FIG. 1.

As best seen in FIGS. 2 and 4, each hinge 28 includes a pivot extending from the rear wall 12c of receptacle 12 comprised of a pair of laterally spaced-apart ears 32 which are connected by an axle 34 and a hook 36 formed integrally with the cover rear wall 24c and arranged to hook around axle 34 as shown in FIG. 4. Each hinge 28 is designed so that its hook 36 can be engaged or disengaged from the corresponding axle 34 only when the cover 24 is swung open more than 180° to the position shown in phantom in FIG. 4. This arrangement assures that the cover 24 will remain attached to receptacle 12 under normal operating conditions for the container, e.g., as when closed or placed open on a horizontal surface for example, but still allows easy assembly and replacement of the cover.

As shown in FIG. 4, the upper edge or lip of receptacle 12 is somewhat rounded and the lower edge of cover 24 is grooved to receive an O-ring 38 which extends all around the cover. Thus, when the cover is in its closed position shown in FIG. 4, the O-ring provides a fluid-tight seal at the boundary between the cover and the receptacle 12.

As best seen in FIGS. 1 and 4, cover 24 may be releasably locked in its closed position by a pair of laterally spaced-apart, collinear, mirror-image latches 42 on the front of housing 10 near the opposite ends thereof. Each latch 42 comprises an actuator 44 slidably mounted to the front wall 24b of cover 24. When an actuator 44 is slid toward the corresponding end of housing 10, it engages under a ramp-like detent 46 (FIG. 3) projecting from the front wall 12b of receptacle 12 thereby wedging the O-ring 38 against the rim of receptacle 12, creating a seal all around the housing. On the other hand, when the two actuators 44 are moved toward one another, they disengage from their respective detents 46 allowing the cover 24 to be swung open to the position shown in FIG. 3.

Referring to FIG. 1, after our sterilization container and its contents have been sterilized, it is essential to know that housing 10 has not been opened up to the time the instruments therein are to be used. Therefore, the present housing includes a safety lock shown generally at 62 removably positioned between the latch actuators 44. The safety lock is basically an elongated, rigid plastic strip 64 having tables 64a extending from its opposite ends. The length of strip 64 substantially is the same as the distance between actuators 44 when those actuators are in their latching positions.

When the strip 64 is placed between the actuators, the tables 64a snap into place under the adjacent actuators thereby securing the strip to the housing 10 so that the actuators 44 cannot be moved to their unlatching positions. The ends of strip 64 are flush with latch actuators 44 and the surface of the strip is nested against the front of housing 10 and is smooth except for a pair of finger holes 66 present near the opposite ends of the strip. Absent these holds 66, it would be very difficult to remove strip 64 without using a special tool.

In accordance with the invention, when a safety lock 62 is installed on housing 10, a patch 68 of paper or other tearable material is adhered to the rear of strip 64 so as to cover the holes 66. Resultantly, once the strip is snapped into place between the latch actuators 44, the strip cannot be removed using one's fingers without punching a hole in at least one of the patches 68. Therefore, when it is time to use the instruments in the sterilization container, the fact that the patches 68 are intact is a good indication that the container has not been opened previously and that its contents are still sterile.

Referring again to FIGS. 1 and 2, housing 10 is designed so that it can be positioned stably in a stack of similar housings. For this, the legs 18 of receptacle 12 and the dimples 26 on cover 24 are positioned relatively so that when two housings 10 are located one over the other, the legs 18 of the upper container are aligned with selected ones of the dimples 26 of the underlying container. Preferably, legs 18 have beveled ends 18a which are arranged to seat snugly in those dimples. Also, ribs 22 are bowed and curved to conform to the three dimensional curvature of the cover top wall 24a, all to maintain the vertical alignment of the housings.

Refer now to FIGS. 3 and 4, our sterilization container also has an assembly inside housing 10 which includes a rectangular microbial filter sheet 72 which is shaped and arranged to cover the bottom wall 12a of receptacle 12 including all of the vent openings 16 therein. Preferably, the receptacle bottom wall 12a is provided with an array of raised pads or standoffs 74 interleaved between the vent openings 16 therein in order to space sheet 72 above openings 16 so that steam can flow through substantially the entire area of sheet 72 rather than through only the portions of the sheet directly opposite openings 16. This assures that steam will flow into the housing 10 in a minimum amount of time.

Figure 5:
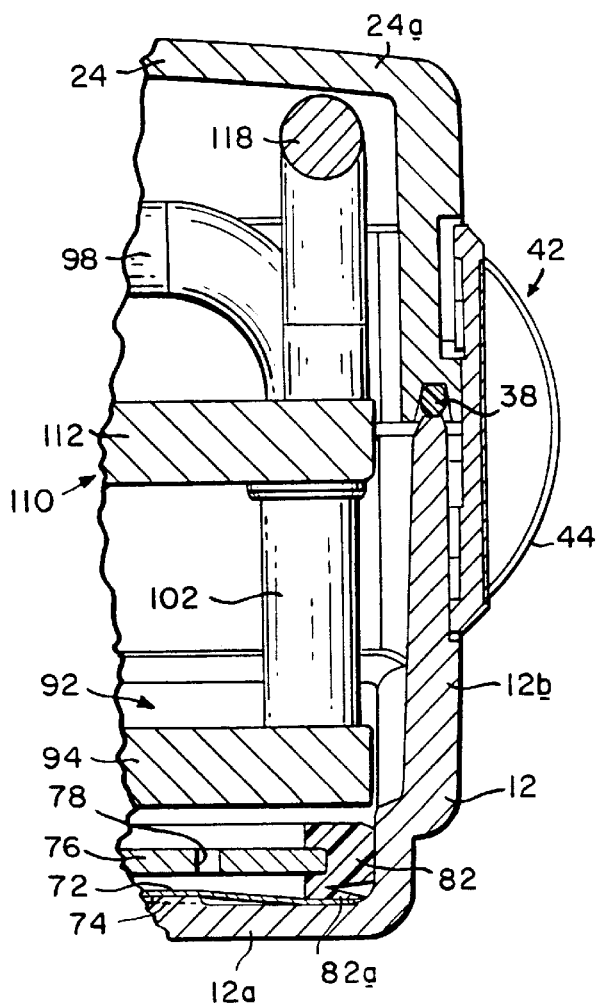
FIG. 5 is a fragmentary sectional view on a larger scale showing a portion of the assembled container in greater detail.

Positioned above sheet 72 is a rectangular metal plate 76 formed with a multiplicity of through-holes 78 distributed in columns and rows over the entire area of the plate. Also, extending around the perimeter of the plate is a frame 82 which may be of rubber or other resilient material molded onto the edge margin of the plate. As best seen in FIG. 5, the frame 82 is formed with a depending, outwardly flaring, fin-like skirt 82a. When plate 76 is positioned in receptacle 12 as shown in FIGS. 4 and 5, the skirt 82a presses against the edge margin of filter sheet 72 and against the bottom wall 12a of section 12 providing a seal between frame 82 and bottom wall 12a. Frame 82 also spaces the plate 76 slightly above the filter sheet 72 as shown.

The holes 78 in the plate 76 should be small enough, e.g., 1/16 in., so that instruments falling onto the plate will not poke through the holes 78 and puncture the filter sheet 72. Their size and distribution should be such that the holes occupy 40–50% of the total area of the plate.

Referring to FIGS. 3 and 4, positioned above metal plate 76 is a lower tray shown generally at 92. Tray 92 consists of a rigid rectangular grid 94, molded of a suitable medical grade plastic material. Grid 94 is formed with columns and rows of relatively large, e.g., 1 in.², square openings or through-holes 96 which are distributed over the entire area of the grid. For reasons to be described later, the walls of each opening 96 are tapered so that the opening is larger at the top of grid 94 than at the bottom thereof.

Tray 92 also includes a pair of inverted, U-shaped handles 98 which extend up from grid 94 at the opposite ends thereof. The handles may be secured to grid 94 by suitable fasteners (not shown). Alternatively, the arms of each handle may be molded as tubes integral with grid 94 with the bridging portion of each handle being formed as a separate member with down-turned ends which may be press fit into the ends of those molded tubes. Also extending up from grid 94 is a plurality, herein four, posts 102. Posts 102 are arranged in pairs at opposite ends of grid 94 inboard handles 98. The end segment of each post 102 has a reduced diameter thereby forming a shoulder 102a more or less midway up along the post. Shoulders 98a are also provided on the arms of handles 98. The shoulders 98a and 102a collectively define a plane spaced above and parallel to grid 94.

Still referring to FIG. 3, the final component of the container is an upper tray shown generally at 110. Tray 110 comprises a rectangular, molded plastic grid 112 which is similar to grid 94 except that it is slightly shorter than grid 94. Like grid 94, it is provided with an array of large square openings 114 with tapered sidewalls. The front and rear edges of grid 112 are provided with laterally spaced-apart notches 116 which, when grid 112 is positioned directly over plate 94, are aligned with posts 102 so that tray 110 can be set down on tray 92 such that grid 112 is supported on the shoulders 98a and 102a of tray 92.

The upper tray 110 also includes a pair of handles 118 similar to handles 98 on tray 92. In this case, however, the handles are mounted at the front and rear edges of grid 112.

To assemble the illustrated container, an appropriately dimensioned filter sheet 72 is set into receptacle 12 so as to cover the bottom wall 12a. As noted previously, the filter is spaced slightly above the bottom wall by the pads 74 so that substantially the entire undersurface of the filter is accessible through the vent openings 16 in the bottom wall 12a. Then, the perforate metal plate 76 is set into receptacle 12 so that its frame 82, or more particularly the frame skirt 82a, contacts and presses down on the edge margin of the filter sheet as shown in FIG. 5. As seen there, the plate 76 is spaced slightly above the filter 72. Then, the lower tray 92 is placed in receptacle 12, the edge margin of that tray resting on frame 82. Finally, the upper tray 110 is placed in position on the shoulders 98a and 102a of tray 92. As noted previously, grid 112 is shorter than tray 92 so that it fits between the handles 98 of the latter tray. In this position, the two trays are spaced parallel one above the other with their openings 96 and 114 being in vertical alignment so that there is a considerable amount of open space in the receptacle 12.

It is important to note that the heights of the posts 102 and the tray handles 98 and 118 are such that when cover 24 is closed as shown in FIG. 4, those posts and handles extend all the way up to the underside of the cover 24. That fact coupled with the previously mentioned resilient skirt 82a on the plate frame 82 ensures that the components of the container inside housing 12 have essentially no vertical play when the cover 24 is closed.

In order to fix the positions of medical instruments on trays 92 and 110, part or all of the grates of either or both trays may be covered by a finger mat 122, a fragment of which is shown on tray 110 in FIG. 3. Preferably, the mat has openings 123 which register with the openings in the underlying grate. Finger mats are well known from U.S. Pat. No. 5,540,901, for example. The mat may have fingers of various heights so the mat can hold instruments of various sizes. For example, the fingers may be shorter near the edges of the mat.

The positions of the medical instruments can also be fixed by means of brackets or fixtures which are arranged to plug into one or more of the openings 96 and 114 in either or both of trays 92 and 110. For example, FIG. 3 illustrates two such fixtures adapted to be plugged into tray 92. One fixture consists of a post 124 having a base 126 with a pair of spaced-apart depending legs 126a. The spacing of the outer walls of the two legs corresponds the dimensions of the openings 96 and 114 in trays 92 and 110 so that the base 26 can be plugged into any one of those openings. As noted previously, the walls of those openings are tapered so that if the post is pressed down into an opening, the legs 126a of its base are squeezed together thereby resiliently retaining the post to the tray.

FIG. 3 also illustrates a channel-type fixture 132 having pairs of depending legs 132a spaced along its length. The channel may be releasably connected to tray 92 (or tray 110) by pressing the pairs of legs into adjacent tray openings. Various other instrument-retaining brackets and fixtures may be provided with legs which plug into one or both of trays 92 and 110. Examples of such fixtures and their uses are disclosed in the above-identified patent and in copending application Ser. No. 08/807,812, filed Feb. 26, 1997, the contents of which are incorporated herein by reference.

After the trays 92 and 110 carrying the various instruments to be sterilized are positioned in the receptacle 12, the cover 24 may be closed and latched by moving the latch actuators 42 laterally toward the ends of the container. This seals the cover to receptacle 12 so that the only fluid entry into housing 10 is through the vent opening 16. Then, the safety lock 62 with its finger holes 66 covered by patches 68 may be snapped into place between the two actuators 44. The locked and sealed container may now be placed in a steam autoclave. During autoclaving, steam enters the container through the vent openings 16 in receptacle bottom wall 12a and is free to pass through substantially the entire area of filter 72 which, as noted previously, is fine enough to exclude microbes and the like. The steam then flows through the holes 78 in the metal plate 76 and through the large openings in the two trays 92 and 110 and circulates around and over the trays so that the steam is rapidly brought into contact with the instruments reposing on the trays. Due to the aforesaid construction of the two trays, the interior of the closed container is quite open so that steam is free to circulate throughout the interior of the container with the result that the instruments are thoroughly sterilized in a minimum amount of time.

If condensation does occur within the container, the resulting condensate is free to drip down onto plate 76 which becomes quite hot during the sterilization process. Resultantly, the plate 76 functions as a heat source which re-evaporates the condensate thus further contributing to the sterilizing of the instruments in the container. In addition, the heated metal plate minimizes the accumulation of moisture at the bottom of receptacle 12 which moisture could wet the filter sheet 72 thus degrading its effectiveness as a microbial filter. In other words, if filter sheet 72 should become overly wet, microbes are more apt to penetrate the filter and the filter itself may become a site for bacterial growth.

At the end of the sterilization cycle, the steam is turned off and the container is exposed to atmospheric pressure while remaining in the autoclave. With this, the radiant heat from the walls of the autoclave penetrates the container and evaporates substantially all of the residual moisture in the container. As a result, assuming the container is not opened, the container contents can remain in a sterilized condition on the shelf for as long as six months or more. When it does become time to use the instruments in the container, it is readily apparent from the condition of safety lock 62 whether or not the container has already been opened so that the container contents are not longer sterile. In other words, if one or both of the patches 68 on lock 62 have been penetrated, that is a good indication that someone has removed and then replaced the lock. This raises the possibility that the container cover 24 has been opened so that the container contents are no longer sterile.

The sterilization container described herein also serves as a convenient means for presenting the instruments that were sterilized in the container. More particularly, the container can be carried to the operating room, clinic or the like and opened after removing the safety lock 62. The trays 92 and 110 can then be removed either together or separately from the receptacle 12 and be placed on a suitable support surface adjacent the patient. The various instruments on the trays are in their original positions due to their aforesaid retention by mat 122 or fixtures 124, 132 so that they may be presented in the order of use for a particular procedure. After the instruments have been used, they may be placed in the receptacle 12 which may then be closed by cover 24 so that there is no danger of those used instruments causing contamination as they are being brought to a disposal or cleaning site.

Figure 6:
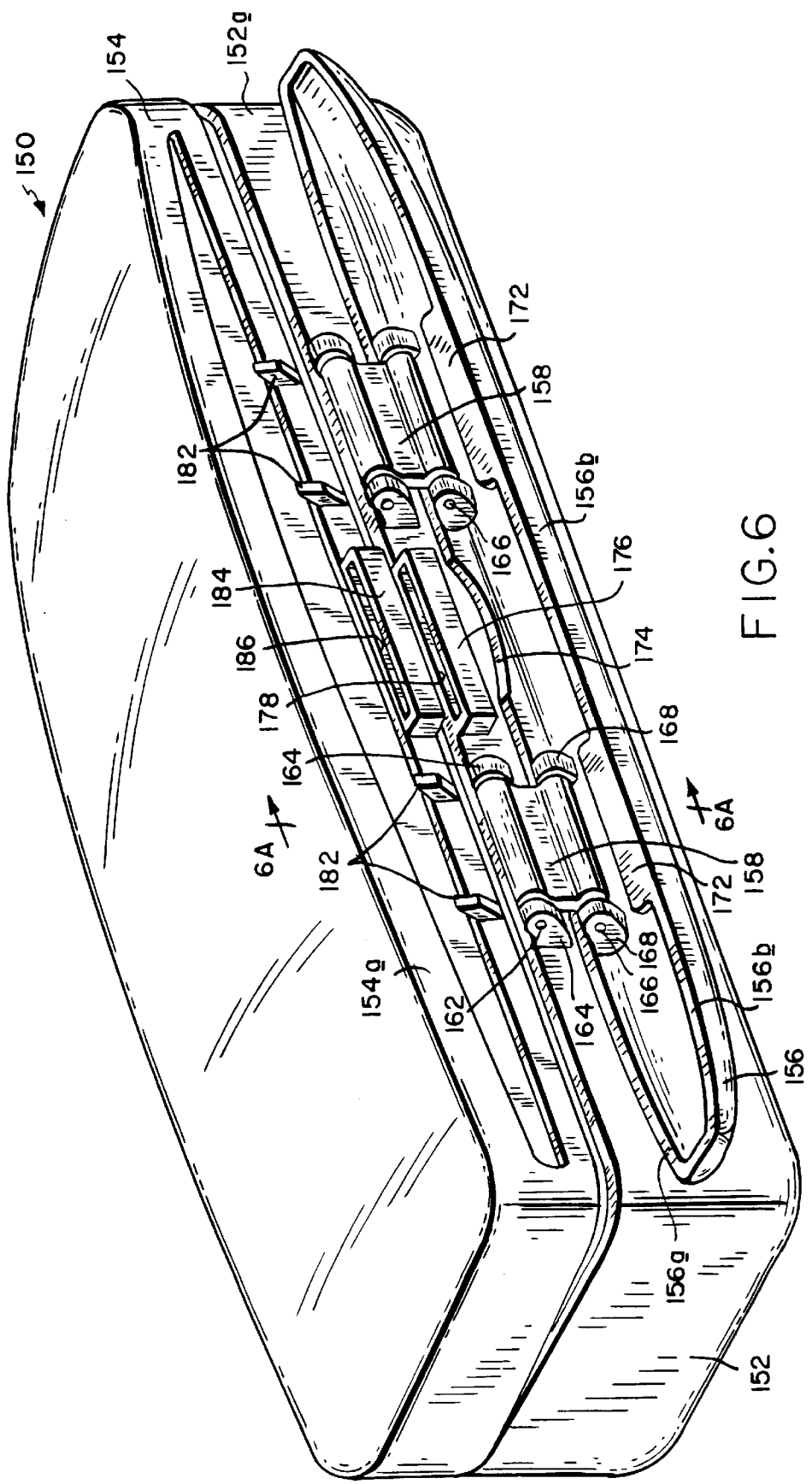
FIG. 6 is a view similar to FIG. 1 showing another container embodiment.

Refer now to FIG. 6 which illustrates a sterilization container with a slightly different latch and safety lock. This container includes a housing shown generally at 150 composed of a rectangular receptacle 152 having a front wall 152a and a cover 154 having a front wall 154a hinged to receptacle 152 in the same manner as the housing discussed above in connection with FIG. 1. A single long latch 156 shaped more or less like a razor clam valve is movably connected to the receptacle front wall 152a by a pair of identical links 158. One end of each link 158 is connected by a pivot pin 162 to a pair of ears 164 projecting from the receptacle front wall 152a. The other end of each link 158 is connected by a second pivot pin 166 to a pair of bosses 168 extending from the rear or lower edge 156a of latch 156 at the interior of the latch. Also, latch 156 is formed with a pair of interior noses 172 located at the front or upper edge 156b of latch 156 directly opposite each pair of ears 168. There is also a rounded notch or recess 174 formed in the latch edge 156b to facilitate opening the latch as will be described.

Also present on the receptacle front wall 152a is a generally rectangular protrusion or boss 176 containing a vertical slot 178 for reasons that will be described later.

The housing cover 154 is formed with two pairs of laterally spaced-apart keepers or detents 182 which project from the cover front wall 154a above the pair of ears 164 in receptacle 152. In addition, a generally rectangular boss 184 with a vertical slot 186 projects from the cover front wall 154a between the pairs of keepers 182. When cover 154 is closed on receptacle 152, the cover boss 184 is located directly above the receptacle boss 176 so that the slots 178 and 186 are in vertical alignment.

Figure 6A:
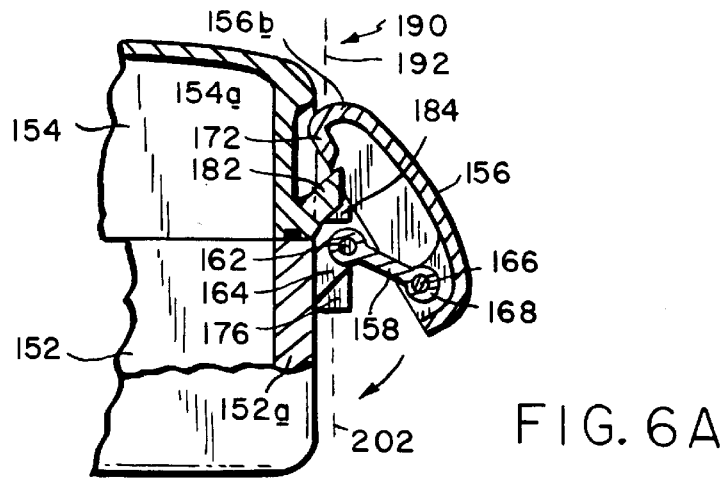
FIGS. 6A and 6B are sectional views showing the operation of the latch mechanism on the FIG. 6 container.
Figure 6B:
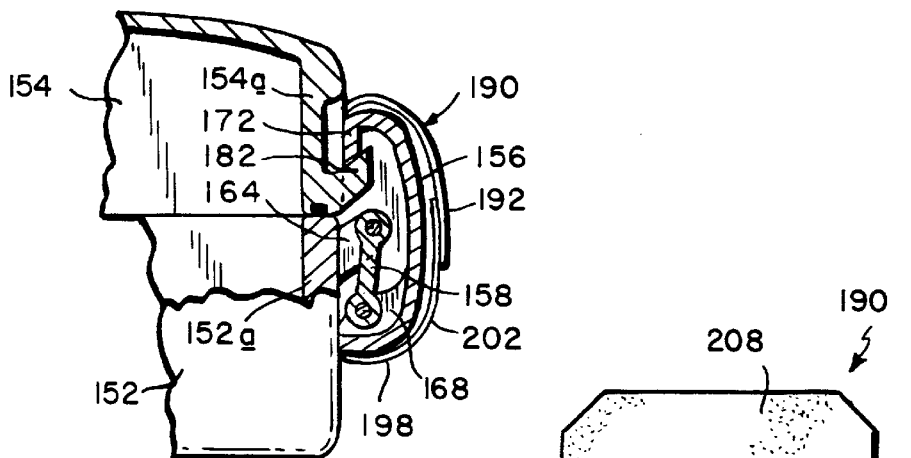

Refer now to FIGS. 6A and 6B, in order to latch and lock housing 150, the cover 154 is swung to its closed position on receptacle 152 as shown in FIG. 6A and the latch 156 is swung up on links 158 so that the noses 172 at the upper edge 156b of the latch engage over keepers 182 projecting from the front wall 154a of receptacle 154 as shown in FIG. 6A. Then, latch 156 is pushed down to the position shown in FIG. 6B. The lengths of the links 158 is such that when the latch is pressed down as aforesaid, links 158 are swung to an over center position which maintains the latch in a stable latched position as illustrated in FIG. 6B.

In order to release the latch 156, the user engages the lower edge of the latch at recess 174 with a finger and lifts that lower edge away from receptacle 152. This swings the links 158 outward to the position shown in FIG. 6A allowing the latch noses 172 to be disengaged from the keepers 182 on the cover by swinging out the upper edge 156b of the latch away from cover 154 so that the cover can be opened.

Figure 7:
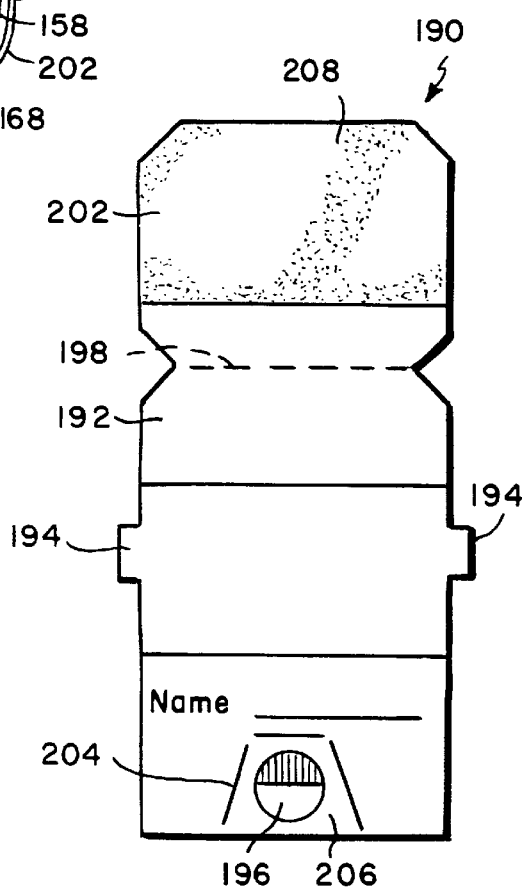
FIG. 7 is a plan view of a lock for the FIG. 1 container.

As with the FIG. 1 sterilization container, it is sometimes essential to know whether or not housing 150 has been opened after having been sterilized. Therefore, housing 150 includes a safety lock shown generally at 190 in FIG. 7. The safety lock is basically a generally rectangular tearable paper or plastic strip whose nominal width is slightly less than the widths of slots 178 and 186 in housing 150. Lock 190 includes a main panel 192 formed with a pair of laterally extending side tabs 194 midway along its length. An area of panel 192 below tables 194 is available to receive printed information and may carry a sterilization indicator 196 which may be a chemically treated spot which changes color when exposed to high temperature steam. Above tabs 194, the panel 192 is joined at a perforated tear line 198 to a smaller auxiliary panel 202. Panel 192 also contains a generally U-shaped cut line 204 that defines a tab 206 connected to panel 192 only at the bottom edge margin of that panel. In addition, an adhesive 208 is applied to the front surface of auxiliary panel 202 or the back surface of panel 192 (or both).

Safety lock 190 may be installed on housing 150 when the housing is in its partially latched condition shown in FIG. 6A. For this, the lock panel 202 is inserted down through the vertically aligned slots 178 and 186 behind latch 156 with the adhesive 208 side of the panel facing the housing as shown in phantom in FIG. 6A until tabs 194 engage the top of cover boss 184. Then, after latch 156 is swung down to its latched position shown in FIG. 6B, the panel 202 is folded up in front of the latch and the free end of panel 192 is folded down over latch over panel 202 so that the two panels are adhered. together by adhesive 208 as shown in FIG. 6B. The adhesive 208 may be a water soluble adhesive or a contact adhesive which requires a similar adhesive area on the underside of panel 92, i.e., like some mailing envelopes.

When lock 190 encircles latch 156 as shown in FIG. 6B, the latch cannot be swung up to its partially open position shown in FIG. 6A without tearing the lock along the tear line 198 which is located right at the lower edge of the latch as shown in FIG. 6B.

On the other hand, if someone should try to peel the adhered panel 192 from panel 198 in an attempt to defeat the lock, the tab 206 would be torn from the remainder of panel 192 so that it would be readily apparent that the lock has been tampered with and that housing 150 may have been opened so that the interior of the housing and its contents may no longer be in a sterile condition.

The housing 150 depicted in FIG. 6 is particularly advantaged in that it has only a single latch which must be manipulated in order to open and latch the housing and its safety lock is a simple inexpensive paper part. Of course, the FIG. 6 housing also has all of the advantages of the one depicted in FIG. 1.

It is apparent from the foregoing that our sterilization container greatly facilitates the sterilizing of medical instruments by enabling the sterilization process to be carried out with maximum speed and efficiency. Yet, the container is for the most part made of a minimum number of plastic parts which can be molded in quantity at relatively low cost. Therefore, the container should find wide acceptance in hospitals and clinics where instruments have to be sterilized on a daily basis.

It will thus be seen that the objects set forth, among those made apparent from the preceding description, are efficiently attained and, since certain changes may be made in the above description without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

Having described the invention, what is claimed as new and secured by Letters Patent is:

1. A sterilization container comprising a receptacle having a front wall, a rear wall and an open top;

a cover having a front wall and a rear wall hinged to the rear wall of the receptacle and swingable between a closed position wherein the cover closes the open top of the receptacle and an open position wherein the cover is positioned to allow access to the interior of the receptacle, and latching means for releasably latching the cover in its closed position, said latching means including a pair of laterally spaced apart, collinear mirror image latches which releasably connect said front walls of the cover and receptacle, each said latch including a detent on the front wall of one of said receptacle and cover, and an actuator slidably mounted to the front wall of the other of said receptacle and cover, said actuators being slidable away from one another to latching positions wherein the actuators are engaged to their respective detents and toward one another to unlatching positions wherein the actuators are disengaged from their respective detents.

2. The container defined in claim 1 and further including safety means removably positioned between said actuators for preventing the actuators from being slid toward their unlatching positions.

3. The container defined in claim 2 wherein the safety means include a rigid strip releasably fixed to the front walls of the cover and receptacle between said actuators, said strip having at least one opening therethrough, and a sheet of finger-penetrable material covering said at least one opening.

4. A sterilization container for medical instruments and the like comprising a receptacle having a front wall, a rear wall and an open top;

a cover having a rear wall hinged to the rear wall of the receptacle and swingable between a closed position wherein the cover closes the open top of the receptacle and an open position wherein the cover is positioned to allow access to the interior of the receptacle;

a latch including a keeper on the front wall of one of said receptacle cover and an actuator swingably connected to the front wall of the other of said receptacle and cover, said actuator being swingable between a latching position wherein the actuator engages the keeper and an unlatching position wherein the actuator is disengaged from the keeper, and safety means connected to at least one of said receptacle and cover and encircling said actuator so that the actuator cannot be moved to said unlatching position without breaking the safety means.

5. The container defined in claim 4 wherein the safety means includes a tearable loop.

6. The container defined in claim 5 wherein the safety means include
   a first slot in the receptacle front wall and wherein the loop extends through the slot.

7. The container defined in claim 6 wherein the safety means also include a second slot in the cover aligned with the first slot when the cover is closed on the receptacle and for receiving the loop.

* * * * *